United States Patent [19]

Gladfelter et al.

[11] Patent Number: 4,649,214

[45] Date of Patent: Mar. 10, 1987

[54] 5(6)-HYDROXYMETHYL-NORBORNANE-2-CARBOXYLIC ACID ESTERS AND POLYURETHANES PREPARED THEREFROM

[75] Inventors: Elizabeth J. Gladfelter, St. Paul; Edgar R. Rogier, Minnetonka, both of Minn.

[73] Assignee: Henkel Corporation, Minneapolis, Minn.

[21] Appl. No.: 676,705

[22] Filed: Nov. 30, 1984

[51] Int. Cl.$^4$ .................. C07C 69/757; C07C 69/753
[52] U.S. Cl. ................................. 560/120; 560/114; 528/74
[58] Field of Search ................................. 560/114, 120

[56] References Cited

U.S. PATENT DOCUMENTS

| | | | |
|---|---|---|---|
| 3,595,917 | 7/1971 | Trecker | 564/454 |
| 3,646,132 | 2/1972 | Trecker | 562/509 |
| 4,218,347 | 8/1980 | Näf | 560/120 |
| 5,492,330 | 1/1970 | Trecker | 526/508 |

FOREIGN PATENT DOCUMENTS 52-57114  5/1977  Japan ..................... 560/120

*Primary Examiner*—C. Warren Ivy
*Attorney, Agent, or Firm*—Ernest G. Szoke; Patrick J. Span

[57] ABSTRACT

Norbornane-2-carboxylic acid esters are disclosed, in particular the 5(6)-formyl and the 5(6)-hydroxymethyl-norbornane-2-carboxylic acid esters. The 5(6)-hydroxymethyl-norbornane-2-carboxylic acid esters may be reacted with polyols to provide a di- or polyfunctional polyol ester suitable for further reaction with polyisocyanates to prepare polyurethanes.

5 Claims, No Drawings

5(6)-HYDROXYMETHYL-NORBORNANE-2-CARBOXYLIC ACID ESTERS AND POLYURETHANES PREPARED THEREFROM

BACKGROUND OF THE INVENTION

This invention is directed to norbornane-2-carboxylic acid esters and in particular to 5(6)-hydroxymethyl-norbornane-2-carboxylic acid esters. These norbornane carboxylic acid esters find utility as intermediates to polyurethanes which are employed as elastomers, coatings and adhesives. Thus, the 5(6)-hydroxymethyl-norbornane-2-carboxylic acid esters can be reacted with polyols to prepare 5(6)-hydroxymethyl-norbornane-2-carboxylic acid polyol esters, which can then subsequently be reacted with polyisocyanates to prepare polyurethanes.

Certain hydroxy-containing norbornane carboxylic acids and esters have previously been known in the chemical literature. Thus, the work of Storm, et al., J.A.C.S. 94:16, pp. 5805–5814, reports the preparation and study of hydroxy-substituted norbornane carboxy compounds to determine the effect of functional group orientation or intramolecular reactions. 2-Hydroxymethyl-bicyclo[2.2.1]heptane-3-carboxylic acid, ethyl ester was prepared as an intermediate in the study of lactonization rates.

It is also known to use hydroxymethyl ester monomers in the preparation of polyurethanes. For example, Peerman, et al., in U.S. Pat. No. 4,423,162 issued Dec. 27, 1983, teaches that hydroxymethyl esters, prepared from naturally occurring fatty oils, can be reacted with polyols and subsequently with polyisocyanates to prepare polyurethanes.

SUMMARY OF THE INVENTION

The present invention is based on the discovery of novel 5(6)-hydroxymethyl-norbornane-2-carboxylic acid esters, which may be reacted with polyols to prepare novel 5(6)-hydroxymethyl-norbornane-2-carboxylic acid polyol esters, and thereafter with polyisocyantes to prepare particularly desirable polyurethanes. These polyurethanes have properties which make them useful as elastomers, coatings and adhesives, especially as hot melt adhesives for flexible substrates such as natural and synthetic rubbers.

The 5(6)-hydroxymethyl-norbornane-2-carboxylic acid esters are prepared according to the following reaction sequence:

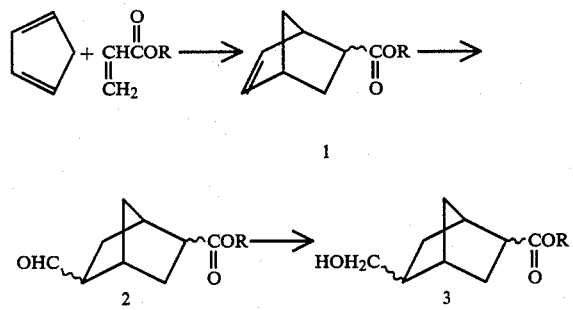

In this reaction sequence, R is selected from the group consisting of alkyl of 1-6 carbon atoms, phenyl and benzyl. The symbol indicates that the ring substituent may be either endo or exo to the ring structure. Compound 2 and 3 may also be defined by the formula

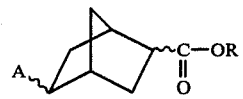

where A is CHO or CH$_2$OH and R is as defined above.

The polyurethanes of the present invention are produced by the reaction of an isocyanate with a polyol of the 5(6)-hydroxymethyl-norbornane-2-carboxylic acid ester of the formula of Compound 3. This polyol is obtained by reaction of the ester defined by formula 3 with at least one polyol, preferably a diol or triol according to the following reaction:

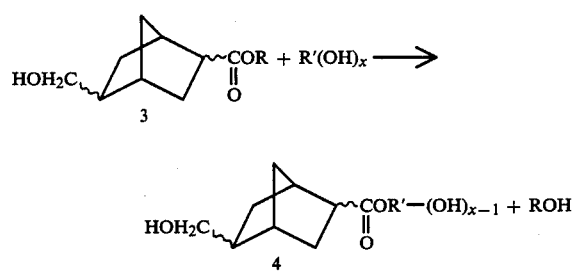

to prepare the 5(6)-hydroxymethyl-norbornane-2-carboxylic acid polyol ester of the formula of Compound 4, wherein R' is the residue of a polyol, x is an integer from 2 to 6 and the symbol indicated that the ring substituents may be either endo or exo to the ring structure. The 5(6)-hydroxymethyl-norbornane-2-carboxylic acid polyol ester of the formula of Compound 4 is then reacted with at least one polyisocyanate.

DETAILED DESCRIPTION OF THE INVENTION

As illustrated in the reaction scheme shown above, norbornane-2-carboxylic acid ester (Compound 1) is prepared by the Diels-Alder reaction of cyclopentadiene with an appropriate acrylic acid ester. The preparation of 5(6)-hydroxymethyl-norbornane-2-carboxylic acid ester (Compound 2) is accomplished by hydroformylation of Compound 1 using either a rhodium or cobalt catalyst. This is followed by hydrogenation of the formyl group of Compound 2 to obtain the hydroxymethyl group of Compound 3 by catalytic methods or by reduction. This reaction sequence is described in detail in U.S. Pat. No. 4,423,162 of Peerman, et al., in U.S. Pat. Nos. 4,216,343; 4,216,344; 4,304,945 and 4,229,562 of Rogier and references discussed therein, and each of these patents and references is hereby specifically incorporated by reference to the extent necessary to support the subject matter of this present invention.

Polyols useful in reacting with the 5(6)-hydroxymethyl-norbornane-2-carboxylic acid ester to prepare the 5(6)-hydroxymethyl-norbornane-2-carboxylic acid polyol esters may be diols, triols, tetrols or even higher polyols. The choice of polyol will depend on the functionality of the product polyol desired for reaction with the isocyanate. The polyol may be represented as R'(OH)$_x$ noted earlier before where R' is the residue of a polyol and x is an integer of 2-6, and generally 2 or 3.

Exemplary of useful polyols are those described in U.S. Pat. No. 4,423,162 of Peerman, et al., earlier incorporated by reference beginning at column 5, lines 43 through column 7, line 43. Preferred materials are the alkylene glycols of 2–6 carbon atoms such as ethylene glycol, neopentylglycol, 1,4-butanediol, and hexane diol. Other diols include those of the formula:

where k is 3; and h+k are non-zero integers, the sum of which is from 12 through 20. An example of such material is 9(10)-hydroxymethyloctadecanol. Additional diol materials which may be used in the present invention include 1,4-bishydroxymethylcyclohexane. Further diol materials include a compound of the formula

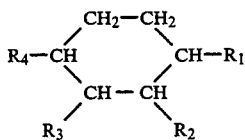

wherein $R_1$, $R_2$, $R_3$ and $R_4$ have a total from 30 to 38 carbon atoms and are each straight-chained alkyl groups having at least 5 carbon atoms, and wherein two of these alkyl groups have omega-hydroxyl substituents. Such later described materials are described in British Patent No. 1,043,507.

Further useful diols which may be utilized in the present invention include compounds of the formula:

and

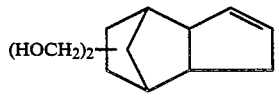

and mixtures thereof. Specific compounds within the scope of the foregoing formulas are 8,8-bis(hydroxymethyl)-tricyclo[5,2,1,0$^{2.6}$]decane and 8,8(9,9)-bis(hydroxymethyl)tricyclo[5,2,1,0$^{2.6}$]dec-2-ene.

Still further diol materials which may be used in the present invention include the 2,5-hexanediol; 1,6-hexanediol; Dimerol alcohol, a 36 carbon diol available from the Henkel Corporation; 1,4-cyclohexazne diol; Polybd R-45hT, a butadiene R-45HT, a butadiene diol having an approximate molecular weight of 2,800; hydrogenated bisphenol A, and other similar materials. An additional diol which may be employed is the diol which is a member selected from the group consisting of 3(4),8(9)-(bishydroxymethyl)tricyclo[5,2,1,0$^{2.6}$]decane.

Suitable triol materials include trimethylol propane and the triols disclosed in U.S. Pat. No. 4,216,344 to Rogier. However, in some instances the presence of secondary hydroxyl groups can cause problems in the properties of the molecules such as sweating wherein the product appears to be wet and not fully cured. Therefore, as a practical matter, triols should contain no secondary hydroxyl groups and/or should preferably contain more than 3 carbon atoms so that any secondary hydroxyl group is not hindered by the close positioning of the primary hydroxyl groups withing the molecule. A suitable example of materials in U.S. Pat. No. 4,216,344 includes 9,9(10,10)-bishydroxymethyloctadecanol.

It is further noted that it is possible to use triols in combinations with other polyols, a particularly valuable blend being that found described by Rogier in U.S. Pat. No. 4,243,818. Additional examples of triols which may be employed include 1,2,6-hexanetriol and other similar materials.

Tetrols include such materials as pentaerythritol. Higher polyols include those pentols described in U.S. Pat. No. 4,216,344 issued to Rogier.

Further polyols which are useful include materials from the work of Rogier in U. S. Pat. No. 4,348,543. Such compounds are shown below

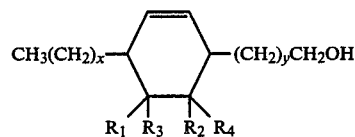

and

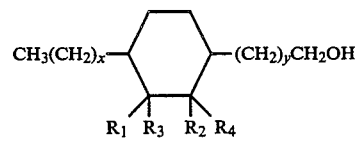

and mixtures thereof wherein $R_1$ and $R_2$ are selected from the group consisting of hydrogen and methyl and mixtures thereof with the provision that one such member must be hydrogen; and $R_3$ and $R_4$ are hydrogen or hydroxymethyl provided that at least one of $R_3$ and $R_4$ are hydrogen or hydroxymethyl provided that at least one of $R_3$ and $R_4$ must be hydroxymethyl, and further that x is an integer of from 3 through 6 and y is an interger from 6 through 9 and that the sum $x+y$ is 12.

Polyols for use in preparing the polyol to be reacted with the isocyanate also include ester linked polyols and ether linked polyols such as tetramethylene glycol ethers. Similarly, diethylene glycol may be employed. It is also possible to use compounds containing both ester and ether linkages within the molecule, provided that at least two hydroxyl radicals remain. A preferred group of polyols within this class of linked polyols are those prepared by condensing a polyol with at least one mole of alkylene oxide per mole of hydroxyl on the polyol. While ethylene oxide is the preferred alkoxylating agent for preparing ether polyols, other alkylene oxides, notably propylene oxide, may be used as well as mixtures of alkylene oxides, most notably mixtures of ethylene and propylene oxides.

The novel 5(6)-hydroxymethyl-norbornane-2-carboxylic acid polyol esters of the invention are prepared by a transesterification reaction. The 5(6)-hydroxymethyl-norbornane-2-carboxylic acid ester is mixed together with a 50% molar excess of the appropriate polyol to favor formation of the 5(6)-hydroxymethyl-norbornane-2-carboxylic acid polyol ester as a 1:1 mole ratio of the reactants. The temperature of the reaction mixture is gradually raised until an alcohol is evolved. The identity of the alcohol generated will, of course, be dependent on the ester moiety of the 5(6)-hydroxymethyl-norbornane-2-carboxylic acid ester. Accordingly, when the ester reactant is a methyl ester, methanol will be evolved. To encourage completion of the transesterification reaction, the alcohol is preferably removed from the reaction mixture as it is formed. It is preferred that no more than a minor amount of starting 5(6)-hydroxymethyl norbornane-2-carboxylic acid ester should remain in the end product, since this acts as a mono-functional material in reactions with polyisocyanates and would therefore act as a chained terminating agent in the reaction to form polyurethanes.

The optimum reaction temperature to produce the 5(6)-hydroxymethyl-norbornane-2-carboxylic acid ester polyol will vary dependent on the catalyst selected for the reaction, if any, and the reactivity of the reactants. Suitable catalysts for this transesterification reaction are described in U.S. Pat. No. 4,423,162, of Peerman, et al., including dibutyl tin oxide, butyltin tris(2-ethylhexoate), butylchlorotin dihydroxide, tetrabutyl orthotitanate, calcium acetate/antimony oxide and base catalysts such as sodium methoxide. Harshaw Ni-5132 P (a supported nickel catalyst containing 64% Ni, available from the Harshaw Chemical Corporation) is an example of an appropriate catalyst for this reaction.

In preparing the 5(6)-hydroxymethyl-norbornane-2-carboxylic acid ester polyol, it is important to avoid the problem of gellation, i.e. the formulation of products of infinitely high viscosity and insolubility in all nondegrading solvents. Gellation can be avoided by limiting the extent of conversion or generally more preferably by using quantities of reactants far from the amounts required stoichiometrically. See Flory, "Principles of Polymer Chemistry," Cornell University Press, 1953, pp. 47, 347.

In preparing polyurethanes acording to this invention, the 5(6)-hydroxymethyl-norbornane-2-carboxylic acid polyol ester is reacted with polyisocyanates. Examples of polyisocyanates which may be used are also described in U.S. Pat. No. 4,423,162, of Peerman, et al., including ethylene diisocyanate, trimethylene diisocyanate, hexamethylene diisocyanate, propylene-1, 2-diisocyanate, ethylidene diisocyanate, cyclopentylene-1, 3-diisocyanate, the 1,2, 1,3- and 1,4-cyclohexylene diisocyantes, the 1,3- and 1,4-phenylene di-isocyanates, the 2,4-and 2,6-tolunene diisocyanates, the 1,3- and 1,4-xylylene diisocyanates, bis(4-isocyanatoethyl) carbonate, 1,8-diisocyanato-p-methane, 1-methyl-2, 4-diisocyanatocyclohexane, the chlorophenylene diisocyanates, naphthalene-1,5-diisocyanate triphenylmethane-4,4', triisocyanate, isopropylbenzene-alpha-4-diisocyante, 5,6-bicyclo[2.2.1.]hept-2-ene diisocyanate, 5,6-diisocyanatobutylbicyclo [2.2.1.]hept-2-ene and similar polyisocyanates.

Also suitable for use are trimethylhexamethylene diisocyanate available from VEBA, heptadecyl (C17) diisocyanate and DDI 1410, an aliphatic C-36 diisocyanate available from the Henkel Corporation of Minneapolis, Minn. (generally such diisocyanates having from 12 to 40 carbon atoms in the aliphatic radical may be used in the present invention).

Of particular interest in the present invention is Isonate 143L diisocyanate, a modified diphenylmethane diisocyanate (MDI) available from Upjohn Corp. Further urethane components are isophorone diisocyanate available from VEBA and Desmodur N, an aliphatic triisocyanate available from Mobay. Dismodur N is more particularly defined as the reaction product of 3 moles of hexamethylene diisocyanate and water having an isocyanate equivalent weight at later defined of 191. Other adducts or prepolymers of the polyisocyanate include Desmodur L and Mondur CB which are the adducts of toluene diisocyanate. The foregoing materials have an isocyanate equivalent weight of approximately 250.

The amount of the polyisocyanate utilized in forming the urethane compositions of the present invention is expressed on a percentage equivalent weight basis with respect to the hydroxyl functionality of the hydroxylmethyl polyol. Desirably, each hydroxy functional group on the polyol will react on a 1:1 stoichiometric basis with the isocyanate functionality of the polyisocyanate compound. It is quite feasible, however, to form the urethane linkage using from about 80% to 120% preferably from about 95% to 105% on a hydroxylisocyanate equivalent basis of the polyisocyanate to form the urethane product. The determination of the amount of polyisocyanate required for a given hydroxymethyl polyol reactant is readily made using hydroxyl or isocyanate equivalent weights as is well known to those of skill in the art. Mixtures of polyisocyanates and hydroxymethyl polyols may also be used in accordance with these parameters.

Cross-linked polyurethanes are obtained whenever the hydroxyl functionality of the polyol reactant is greater than 2.0. Otherwise, thermoplastic polyurethanes are obtained.

To form the urethane reaction product, the hydroxymethyl polyol and the organic polyisocyanate reactants are mixed together in the proper proportions. When utilized as a coating, the compounds are then quickly spread with a knife blade, brush or spray over the surface of the article to be coated. Where molded articles are desired various techniques such as casting, injection molding, reaction injection molding may be employed.

If desired, various urethane catalysts may be employed to promote the reaction. Examples of such urethane catalysts include triethylene diamine, N-ethylmorpholine, dimethyl piperazine, triethylamine, N,N,N',N'-tetramethylbutane-1,3-diamine, dibutyltin dilaurate, stannous octoate, stannous oleate, and stannous tallate, as well as other art recognized urethane catalysts. Typical levels of the urethane catalyst are from about 0.001% to about 5% by weight of the urethane components. A suitable catalyst according to this invention is FASCAT 4102, a butyl tin tri(2-ethylhexoate) catalyst available from M & T Chemicals, Inc.

Trimerization catalysts such as diethylene diamine and BF$_3$ derivatives, can be included in the reaction mixture to convert the polyisocyanates to polyisocyanurates in situ and then to polyurethanes.

One or more additional polyols may be included in the reaction mixture to modify the properties of the resulting polyurethane, principally hardness and elasticity. Short chain polyols act as hard segment contributors to increase elastomer hardness while long chain polyols act as soft segment contributors to enhance the elastic properties of the elastomer. Such modifying polyols include alkyl or cycloalkyl polyols, ester linked polyols, ether linked polyols, ether and ester linked polyol and hydroxy functional acrylic copolymers.

Specific examples of the alkyl and cycloalkyl polyols include 2,5-hexanediol, 1,6-hexanediol, ethylene glycol, glycerol, 1,2,6-hexanetriol, pentaerythritol, 1,4-cyclohexane diol, and 1,4-butanediol.

Examples of ester linked saturated polyols include Niax PCP0200 and PCP0240 both available from Union Carbide and having respective molecular weights of approximately 530 and 2000. Both of the foregoing compounds are diols. Niax PCP0300 also available from Union Carbide is a caprolactoneester triol having an approximate molecular weight of 540. Niax PCP0310 also available from Union Carbide is a caprolactone ester triol having a molecular weight of approximately 900. Especially suitable modifying polyols in preparing the instant polyurethanes are long chain ether polyols, particularly Teracol 1000, a polytetramethylene ether glycol of approximate molecular weight of 1,000, available from DuPont. Further ether linked saturated polyols useful in the present invention includethe Polymeg Q0650, Q0100 and Q0200 all of which are ether diols available from Quaker having a respective molecular weight of approximately 650, 1000 and 2000. Pluracol P1010 having an approximate molecular weight of 1050 available from Wyandotte is an example of polypropylene oxide ether linked diol useful in the present invention. Similar Wyandotte products useful as saturated polyols in the present invention include Pluracol TP440 and 150 which are propylene oxide ether linked triols having respective molecular weights of approximately 425 and 1560. In similar fashion Pluracol GP3030 is another saturated polyol suitable for the present invention available from Wyandotte. The foregoing material is a glycerine polypropylene ether linked triol having an approximate molecular weight of 2900.

Additional Pluracols useful in the present invention include Pluracol PEP450 which is a pentaerythritol polypropylene oxide ether linked tetrol having a molecular weight of 405 and Pluracol 493 an ether linked tetrol having a molecular weight of approximately 3630.

In addition, polyols having hydroxyl functionalities greater than 2.0 may be included in the reaction mixture as cross-linking agents. Illustrative of some suitable polyols for this purpose are those disclosed in U.S. Pat. No. 4,216,344 issued Aug. 5, 1980 to Rogier. Additional materials which may be used as cross-linking agents are found in the appliation of Rogier, Ser. No. 233,793, filed Feb. 12, 1981, now U.S. Pat. No. 4,348,543.

In mixing the 5(6)-hydroxymethyl-norbornane-2-carboxylic acid polyol ester and the polyisocyanate reactants, additional heating is only required where lower viscosity for efficient mixing is desired. For convenience the reactants may be heated to the temperature of reaction typically from about 0° to about 110° C., preferably from about room temperature, i.e., 22° C. to about 85° C. The system is operated under a high vacuum to degas the reaction mixture for about 15 minutes. The reaction mixture is then cured for a time period of from about one to twenty-four hours depending upon the curing temperature and the particular polyurethane formed. Optimum curing cycles can be readily determined without undue experimentation by those of skill in the art.

Polyurethanes of the invention may also be prepared as isocyanates terminated pre-polymers by conducting the reaction with a substantial excess of polyisocyanate and not curing the reaction mixture. The pre-polymer provides an intermediate form of the polyurethane which is more convenient to handle than the individual reactants. By mixing the pre-polymers with additional polyol and curing the prepolymer is converted to a polyurethane resin.

The polyurethanes prepared in accordance with the present invention exhibit a desirable combination of properties particularly in the combination of tensile strength and elongation. In many respects, the products provide properties similar to those prepared from polycaprolactone polyester polyols. They are particularly useful for a wide range of application as elastomers, protective coatings and adhesives.

The following examples are provided for illustrating various aspects of the present invention. These examples are purely illustrative, and it is to be understood that they are not intended to place any limitations on the scope of the present invention.

EXAMPLE 1

3 g. of cyclopentadiene and 4.3 g. of methylacrylate (equimolar amounts) were combined together in a vessel fitted with a reflux condenser and a magnetic stirrer. The initial reaction temperature was 22° C. and at the end of 5 hours analysis by gas chromatography indicated that the yield of norbornene carboxylic acid, methylester was greater than 90%. The proton NMR spectrum of this compound was consistent with the structure shown for Compound 1 hereinabove where R is methyl.

EXAMPLE 2

To 330 g. of toluene was added 330 g., 2.17 moles, of norbornene carboxylic acid, methylester, prepared in similar manner to Example 1, and 0.25 g. of triphenyl phosphite and a rhodium catalyst (50 ppm Rh). The reaction system employed consisted of a one liter autoclave fitted with internal heating-cooling coils, magnadrive stirrer, thermocouple and sample discharge line. A 2.113 liter pressure ballast of 1,500 psi pressure was used as a source for introducing hydrogen-carbon monoxide gas into the reaction mixture. The pressure ballast was pressurized to approximately 4,000 psi initial pressure and ended with a final pressure of approximately 3,000 psi. The pressure drop was recorded by a pressure transmitter connected to a chart recorder and also by sight readings at time intervals into the reaction. The final reaction conditions were set at 93° C.; 1,250 rpm, and 900 psi. The product of this hydroformylation reaction was 5(6)-formyl-norbornane-2-carboxylic acid, methyl ester, the structure shown for Compound 2 hereinabove, where R is methyl. The structure of this product was confirmed by proton NMR.

EXAMPLE 3

The Example shows the hydrogenation of 5(6)-formylnorbornane-2-carboxylic acid, methyl ester of Example 2 to prepare the corresponding 5(6)-hydroxymethyl-norbornane-2-carboxylic acid, methyl ester.

To 160 g. of methanol was added 160 g., 0.89 moles, of 5(6)-formyl-norbornane-2-carboxylic acid, methyl ester, and 16 grams of a catalyst, Harshaw Ni 5132P Lot 136, available from the Harshaw Chemical Company. The reaction system used consisted of a 1 liter autoclave fitted with internal heating-cooling coils, magnadrive stirrer, thermocouple and sample tube. A 2.113 liter pressure ballast capable of 1,500 psi pressure was used to introduce hydrogen gas into the reaction mixture. The pressure ballast was initially pressured to approximately 4,000 psi and ended with a final pressure of approximately 3,400 psi. The pressure drop was recorded by a pressure transmitter connected to a chart recorder and also by sight readings at time intervals during the course of the reaction. Reaction conditions were set at 120° C.; 1,250 rpm and 800 psi. The cessation of pressure drop and a leveling off of balast pressure to a constant reading indicated the completion of the reaction.

The NMR and IR spectra were both consistent with the structure shown for Compound 3 where R is methyl. After distillation the hydroxyl equivalent weight was 183.1 with the theoretical being 184.2. The saponification equivalent weight was 186.2 with the theometical being 184.2. C,H,O analysis: (Theoretical) Observed C: (65.2), 64.5; H: (8.8), 9.0, O: (26.1), 26.2.

EXAMPLE 4

117.0 g., 0.639 moles, of 5(6)-hydroxymethyl-norbornane-2-carboxylic acid, methyl ester were reacted with 86.26 g., 0.9585 moles, of 1,4-butanediol by stirring in a vessel equiped with a heating source and a distillation take-off with a short Vigreaux column. Distillate began to come over at 188° C. Temperature was increased over 2.5 hours to 200° C, where it was maintained for 3.5 hours, at which point 15.5 mls. of distillate had been collected. The temperature was raised to 233° C. over the next 5 hours, after which time 22 mls. of distillate had been collected. The product was stripped by heating at 138° -173° C. under 0.025-2.1 mm Hg over a period of 2½ hours. Analysis by gas chromatography showed a 5.3% of residual starting 5(6)-hydroxymethyl-norbornane-2-carboxylic acid, methyl ester.

The analyzed equivalent weight of the transesterification product was 170 and the viscosity was 150 poise at 70° F.

The following examples illustrate the preparation of polyurethanes from 5(6)-hydroxymethyl-norbornane-2-carboxylic acid polyol esters. It is to be understood that these examples are purely illustrative and serve in no way to limit the scope of the present invention. The elastomer properties of these polyurethanes were determined in accordance with the following elastomer test procedures:

Durometer Hardness, ASTM D 2240
Ultimate Tensile Strength=Maximum Tensile Stress, either yield or break, during test, ASTM D 412
Percentage Elongation at Break, ASTM D 412
Set After Break=Percantage of unrecovered stretch in a sample 10 minutes after testing to failure in tension
Split Tear=Tear Strength of a sample 0.125 inch or less, 75×25 mm, carefully split 50 mm and pulled at 180° C. and calculated in lbs. per inch of thickness, ASTM D 1938.
Compression Set =the percentage of unrecovered height of a cylindrical specimen compressed 25% of its height at 70° C. for 22 hours, measured ½ hour after release, ASTM D 395, Method B, Type 1
Water Absorption=the percentage weight gained in a 0.125 inch thick specimen after 24 hours in water at 70° C., ASTM D 570, 70° C. H$_2$O, 24 hours.
Hydrolytic Stability=Percentage of original tensile strength of sample, dried after subjection to 18 hours at 125° C., 14 psi steam, SATRA Method, 14 psi, 125° C. steam.
Stiffness Value=T$_f$/T$_4$, ASTM D 1043
T$_f$, ° C.=the temperature at which the torsional modulus equals 45,000 psi.
T$_4$, ° C.=the temperature at which the torsional modulus equals 3,333 psi.

EXAMPLE 5

The ester polyol product of Example 4 was used to prepare a thermoplastic polyurethane elastomer. It was blended with a modifying polyol and reacted with a polyisocyanate as follows:

TABLE I

|  | Equiv. | Grams | Wt. % |
| --- | --- | --- | --- |
| Ester polyol of Example 4 | 0.03 | 5.11 | 39.34 |
| Modifying polyol Teracol-1000 (a polyoxy tetramethylene glycol of MW near 1000) | 0.005 | 2.66 | 20.4 |
| Isonate 143 L diisocyanate (a modified diphenyl methane diisocyanate (MDI) containing a high percentage of MDI and a lesser amount of polycarbodiimide adducts) | 0.036 | 5.22 | 40.2 |

The polyols were blended and degassed, and the polyisocyanate was added. While blending under vacuum, the exotherm of the reaction rose to 90° F. (32° C.). After 5 minutes, the reaction mixture was poured into molds prepared with a release agent and cured for 24 hours at 100° C. The Durometer Hardness of the resulting elastomer was measured at 72 C.

EXAMPLE 6

The hydroxymethyl ester polyol of Example 4 was used to prepare the following polyurethane. Blending with a polyol and reaction with a polyisocyanate were carred out as follows:

TABLE II

|  | Equiv. | Grams | Wt. % |
| --- | --- | --- | --- |
| Ester polyol of Example 4 | 0.2 | 3.41 | 28.8 |
| Modifying polyol Teracol-1000 | 0.08 | 4.25 | 35.9 |
| Isonate 143 L Diisocyanate | 0.287 | 4.17 | 35.2 |

After blending the polyols, the reaction mixture was degassed until bubbling stopped and then the diisocyanate was added. After blending for a further 9 minutes under vacuum, the vacuum was broken and the reaction mixture was poured into molds prepared with a release agent and cured for 24 hours at 100° C. The Durometer Hardness of this elastomer was 58 D.

EXAMPLE 7

A polyurethane was prepared from the hydroxymethyl ester polyol of Example 4 in the following manner:

TABLE III

|  | Equiv. | Grams | Wt. % |
| --- | --- | --- | --- |
| Ester polyol of Example 4 | 0.26 | 44.28 | 25.8 |
| Modifying polyol Teracol-1000 | 0.13 | 69.07 | 40.3 |
| Isonate 143 L Diisocyanate | 0.40 | 58.16 | 33.9 |

The polyols were weighed into a vessel and heated under N$_2$ gas, while stirring, to 70° C. The polyol mixture was degassed, cooled to 30° C., and the isocyanate was added with increased stirring of the reactants. After blending for 12 minutes under vacuum the exotherm of the reaction increased to 65° C., at which point the vacuum was broken and the reaction mass was poured into prepared molds, which were then pressed at 100° C. and 10,000 psi for 35 minutes until set. The molds were then put into a curing oven at 100° C. for 24 hours.

The elastomer has the following properties:

Durometer Hardness—90 A 42D
Ultimate Tensile Strength, psi—5990
Elongation at Break, Percentage—360
Set After Break Percantage—4.0
Split Tear—187 lbs.
Compression Set, Percentage—91
Water Absorption, 24 hrs. at 70° C., Percentage—2.0
Hydrolytic Stability, Percent retained ultimate tensile strength—79
Stiffness Value—$T_f/T_4$
  $T_f$, degrees Centigrade = −9
  $T_4$, degrees Centigrade = +6.5

It is apparent from the details of the foregoing description and Examples that the 5(6)-hydroxymethyl-norbornane-2-carboxylic acid esters of this invention may be formulated into a wide variety of their corresponding polyol esters and, ultimately, into an even wider variety of polyurethane elastomers. While the present invention has been described and examplified in terms of certain preferred embodiments, those of skill in the polymer art will readily appreciate that a variety of modifications, changes, omissions, and substitutions can be made without departing from the essence of the instant invention. The scope of the present invention is therefore intended to be limited solely by the following claims.

We claim:

1. A norbornane-2-carboxylic acid ester of the formula:

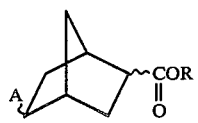

wherein A is CHO and R is selected from alkyl of 1–6 carbon atoms, phenyl, or benzyl.

2. A compound according to claim 1 wherein R is methyl.

3. A 5(6)-hydroxymethyl-norbornane-2-carboxylic acid polyol ester of the formula:

wherein R' is the residue of a polyol and x is an integer of 2 to 6.

4. A polyol ester according to claim 3, wherein x is 2 and R' in the residue of a diol.

5. A polyol ester according to claim 4, wherein said diol is 1,4-butanediol.

* * * * *